United States Patent [19]

Iwakiri et al.

[11] Patent Number: 4,988,428
[45] Date of Patent: Jan. 29, 1991

[54] NOX CONCENTRATION MEASURING APPARATUS

[75] Inventors: Yasunori Iwakiri; Akinobu Moriyama, both of Yokohama, Japan

[73] Assignee: Nissan Motor Company, Ltd., Japan

[21] Appl. No.: 523,459

[22] Filed: May 15, 1990

[30] Foreign Application Priority Data

Jun. 1, 1989 [JP] Japan ................................ 1-140016

[51] Int. Cl.⁵ ......................................... G01N 27/407
[52] U.S. Cl. .................................... 204/406; 123/489; 204/153.14; 204/410
[58] Field of Search ................... 204/410, 406, 153.14; 123/489; 60/276

[56] References Cited

U.S. PATENT DOCUMENTS 4,115,235 9/1978 Capone ............................... 204/410
4,927,517 5/1990 Mizutani et al. .................... 204/406

FOREIGN PATENT DOCUMENTS 2-1543 1/1990 Japan .

Primary Examiner—G. L. Kaplan
Attorney, Agent, or Firm—Lowe, Price, LeBlanc, Becker & Shur

[57] ABSTRACT

An NOx concentration measuring apparatus employing first and second wide-range air/fuel ratio sensors for measuring an NOx concentration of gases introduced thereto through a first passage. First and second restricted orifices are provided in the first passage upstream of the first and second sensors. A second passage is connected to the first passage between the first and second orifices. A suction pump is connected to the first passage downstream of the first and second sensors for producing a suction vacuum in the first passage and is also connected to the second passage for producing a suction vacuum in the second passage. The first and second orifices are effective to prevent momentary gas pressure fluctuations from affecting the accuracy of measurement of the first and second sensors.

3 Claims, 4 Drawing Sheets

NOX CONCENTRATION MEASURING APPARATUS

BACKGROUND OF THE INVENTION

This invention relates to an NOx concentration measuring apparatus utilizing two wide-range air/fuel ratio sensors.

For example, Japanese patent application No. 63-122707 describes an NOx concentration measuring apparatus which utilizes two wide-range air/fuel ratio sensors. The first sensor is sensitive to oxides of nitrogen for resolving oxides of nitrogen at low oxygen partial pressures. The first sensor includes an electrochemical cell containing an oxygen ion conductive electrolyte layer having two electrodes disposed on the opposite surfaces thereof for producing a first sensor signal indicative of an oxygen partial pressure of the gases introduced into the electrochemical cell. The second sensor is insensitive to oxides of nitrogen. The second sensor includes an electrochemical cell containing an oxygen ion conductive electrolyte layer having two electrodes disposed on the opposite surfaces thereof for producing a second sensor signal indicative of an oxygen partial pressure of the gases introduced into the electrochemical cell. The first and second sensor signals are used in calculating the NOx concentration of the gases introduced into the electrochemical cells of the first and second sensors.

The first and second sensors are located in the exhaust manifold of an internal combustion engine for measuring the NOx concentration of the exhaust gases discharged from the engine. However, the exhaust manifold pressure fluctuates greatly to affect the accuracy of the NOx concentration measurement of the first and second sensors during engine operation.

SUMMARY OF THE INVENTION

It is, therefore, a main object of the invention to provide an improved NOx concentration measuring apparatus which can prevent gas pressure fluctuations from affecting the NOX concentration measurement accuracy.

There is provided, in accordance with the invention an apparatus for measuring an NOx concentration of gases to be measured. The apparatus comprises first and second sensors. The first sensor is sensitive to oxides of nitrogen for resolving oxides of nitrogen at low oxygen partial pressures. The first sensor includes an electrochemical cell containing an oxygen ion conductive electrolyte layer having at least two electrodes disposed on the opposite surfaces thereof for producing a first sensor signal indicative of an oxygen partial pressure of the gases introduced into the electrochemical cell. The second sensor is insensitive to oxides of nitrogen. The second sensor includes an electrochemical cell containing an oxygen ion conductive electrolyte layer having at least two electrodes disposed on the opposite surfaces thereof for producing a second sensor signal indicative of an oxygen partial pressure of the gases introduced into the electrochemical cell. The first and second sensors are connected to means for calculating an NOx concentration based on the first and second sensor signals. The apparatus also includes a first passage for introducing gases into the electrochemical cells of the first and second sensors. First and second restricted orifices are provided in the first passage upstream of the first and second sensors for restricting a gas flow to the first and second sensors. A second passage is connected to the first passage between the first and second orifices, and a suction pump connected to the first passage downstream of the first and second sensors for producing a suction vacuum in the first passage and to the second passage for producing a suction vacuum in the second passage.

In another aspect of the invention, there is provided an apparatus for measuring an NOx concentation of exhaust gases discharged into an exhaust manifold from an internal combustion engine. The apparatus comprises first and second sensors. The first sensor is sensitive to oxides of nitrogen for resolving oxides of nitrogen at low oxygen partial pressures. The first sensor includes an electrochemical cell containing an oxygen ion conductive electrolyte layer having at least two electrodes disposed on the opposite surfaces thereof for producing a first sensor signal indicative of an oxygen partial pressure of the exhaust gases introduced into the electrochemical cell. The second sensor is insensitive to oxides of nitrogen. The second sensor includes an electrochemical cell containing an oxygen ion conductive electrolyte layer having at least two electrodes disposed on the opposite surfaces thereof for producing a second sensor signal indicative of an oxygen partial pressure of the exhaust gases introduced into the electrochemical cell. The first and second sensors are connected to means for calculating an NOx concentration based on the first and second sensor signals. The apparatus also includes a first passage opening into the exhaust manifold for introducing exhaust gases into the electrochemical cells of the first and second sensors. First and second restricted orifices provided in the first passage upstream of the first and second sensors for restricting a gas flow to the first and second sensors. A second passage is connected to the first passage between the first and second orifices, and a suction pump connected to the first passage downstream of the first and second sensors for producing a suction vacuum in the first passage. The suction pump is connected to the second passage for producing a suction vacuum in the second passage.

BRIEF DESCRIPTION OF THE DRAWINGS

This invention will be described in greater detail by reference to the following description taken in connection with the accompanying drawings, in which.

DETAILED DESCRIPTION OF THE INVENTION

Figure 1:
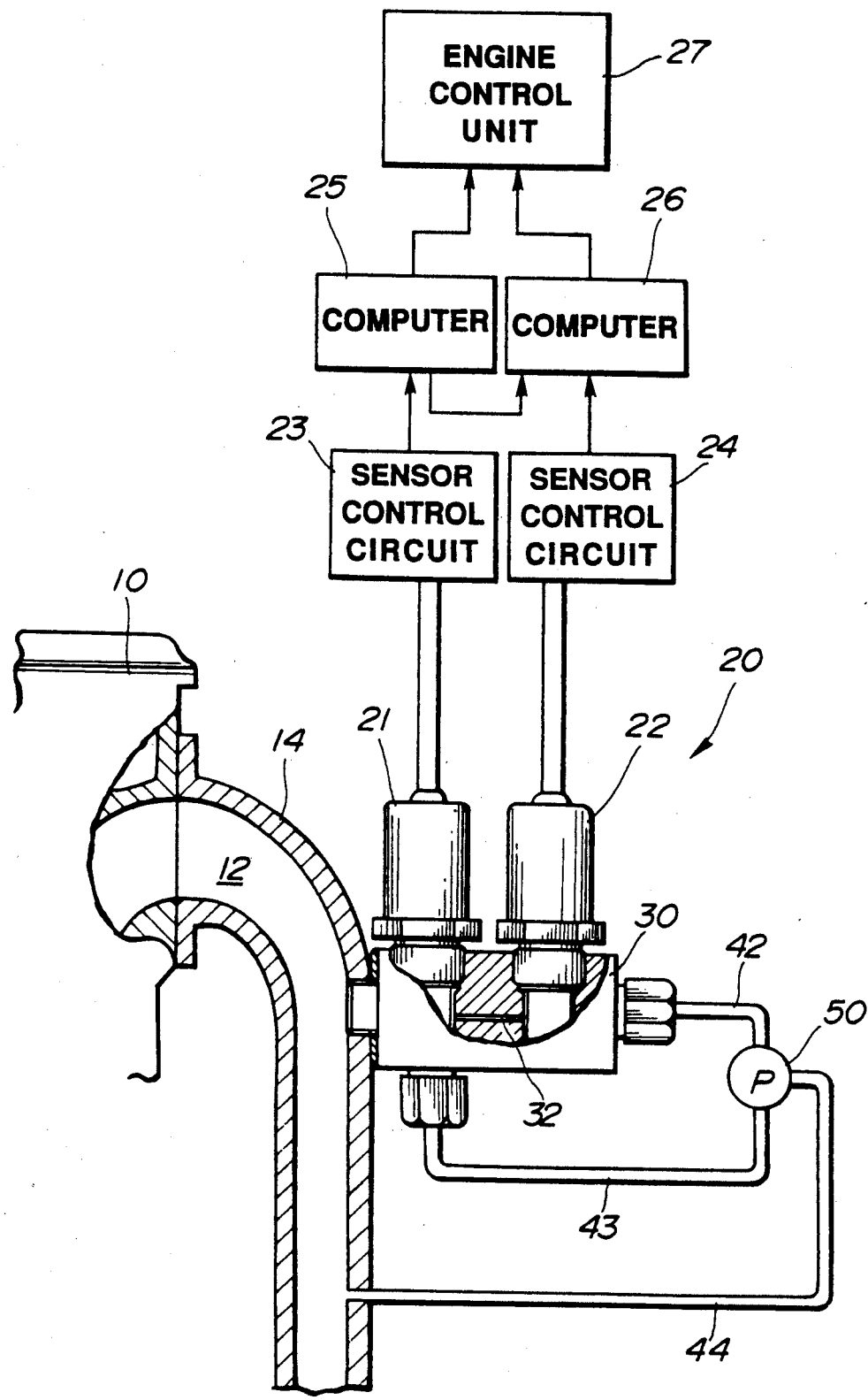
FIG. 1 is a schematic diagram showing an NOx measuring apparatus made in accordance with the invention.

With reference to the drawings wherein like numerals refer to like parts in the several views, and in particular to FIG. 1, there is shown a portion of an internal combustion engine 10 for which an NOx concentration measuring apparatus according to the invention is used. The engine 10 has an exhaust manifold 12 into which exhaust gases are discharged from the engine. The exhaust gases are then discharged to the atmosphere through an exhaust system (not shown) which conventionally includes a muffler and an exhaust pipe.

The NOx concentration measuring apparatus, generally designated by the numeral 20, is shown as including first and second sensors 21 and 22. The first sensor 21 may be taken in the form of a wide-range air/fuel ratio sensor of the type sensitive to oxides of nitrogen (Nox) for measuring the existing oxygen partial pressure. This type of air/fuel ratio sensor has a capacity of resolving NOx only at low oxygen partial pressures. The first sensor 21 includes an electrochemical cell containing an oxygen ion conductive electrolyte layer having at least two electrodes disposed on the opposite surfaces thereof for producing a first sensor signal indicative of an oxygen partial pressure of the exhaust gases introduced into the electrochemical cell. The second sensor 22 may be taken in the form of a wide-range air/fuel ratio sensor of the type insensitive to oxides of nitrogen (NOx) for measuring the existing oxygen partial pressure. This type of air/fuel ratio sensor cannot resolve NOx regardless of the oxygen partial pressure. The second sensor 22 includes an electrochemical cell containing an oxygen ion conductive electrolyte layer having at least two electrodes disposed on the opposite surfaces thereof for producing a second sensor signal indicative of an oxygen partial pressure of the exhaust gases introduced into the electrochemical cell.

The first sensor 21 converts the concentration of oxygen (O2), carbon monoxide (CO), hydrogen (H2), hydrocarbon (HC), nitrogen monoxide (NO) and other constitutents contained in the exhaust gases into a corresponding O2 concentration and it produces a first sensor signal having a value proportional to the converted O2 concentration. The second sensor 22 converts the concentration of oxygen (O2), carbon monoxide (CO), hydrogen (H2), hydrocarbon (HC), and other constituents except for oxides of nitrogen into a corresponding O2 concentration and it produces a second sensor signal having a value proportional to the converted O2 concentration. Thus, the second sensor 22 is substantially the same as the first sensor 21 except that it is insensitive to oxides of nitrogen (NOx). The first and second sensors 21 and 22 are connected respectively to the first and second sensor control circuits 23 and 24.

Figure 2:
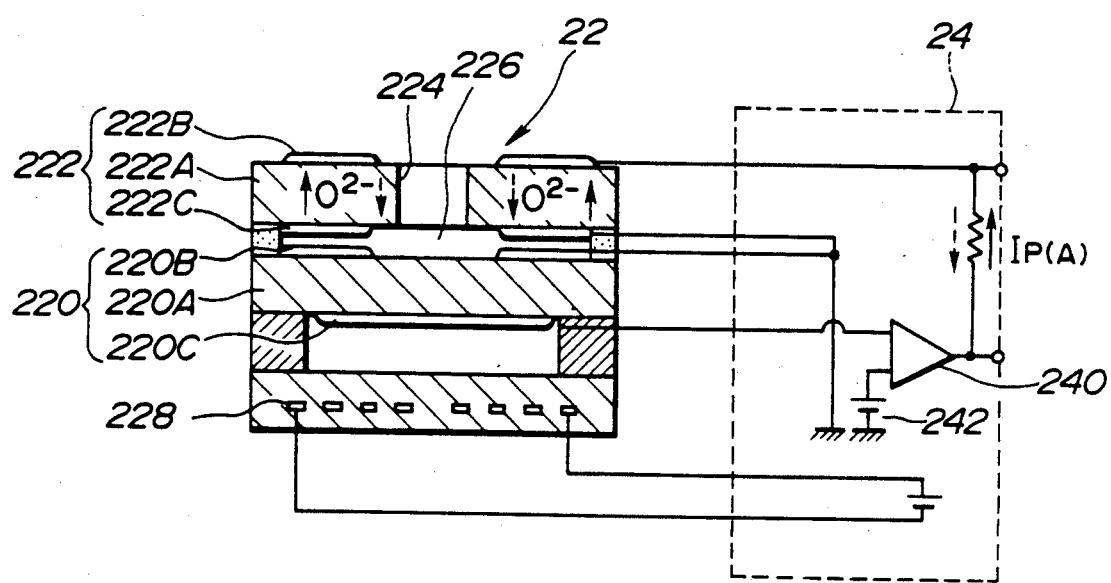
FIG. 2 is an enlarged sectional view of the electrochemical cell of the second sensor.

Referring to FIG. 2, the second sensor 22 includes at least one pair of sensing and pumping cells 220 and 222 disposed in a parallel-spaced relation with respect to each other within a diffusion chamber 224. The sensing cell 220 includes electrodes 220B and 220C disposed on the opposite side surfaces of a solid electrolyte layer 220A. The electrodes 220B and 220C of the sensing cell 220 is formed of a material such as platinum or the like insensitive to NOx. The pumping cell 220 includes electrodes 222B and 222C disposed on the opposite side surfaces of a solid electrolyte layer 222A. Exhaust gases are introduced through a port 224 into the diffusion chamber 226. The numeral 228 designates a heater element. The second sensor 22 is connected to a sensor control circuit 24 which includes a differential amplifier 240 having an input connected to the electrode 220C and another input connected to a reference voltage source 242. The electrode 220B is grounded. The differential amplifier 240 has an output connected to the electrode 222B. The electrode 222C is grounded. The control circuit 24 controls the current to the heater element 228 and the current Ip to the electrode 222B so as to maintain the voltage between the electrodes 222B and 222C sandwiching the solid electrolyte layer 222A of the pumping cell 222 at a constant value. As a result, the oxygen concentration is reduced substantially to zero within the diffusion chamber 226 and the exhaust gases charged in the diffusion chamber 226 is maintained substantially at the stoichiometric air/fuel ratio value. The current Ip to the electrode 222B has a value corresponding to the O2 concentration. The control circuit 23 for the first sensor 21 is substantially similar to the control circuit 24. The first and second sensors 21 and 22 are described in detail, and are incorporated herein by reference, in Japanese patent application No. 63-122707.

Returning to FIG. 1, the first and second sensor signals are fed from the first and second sensor control circuits 23 and 24 to first and second computers 25 and 26, respectively. The first computer 25 calculates a value of the air/fuel ratio of the exhaust gases based on the value of the first sensor signal fed thereto from the first sensor control circuit 23 and transfers the calculated air/fuel ratio value to an engine control unit 27. The first computer 25 also transfers the first sensor signal fed thereto from the first sensor control circuit 23 to the second computer 26. The second computer 26 calculates an O2 concentration value, which is one-half of the NO concentration, as a function of a difference between the values of the first and second sensor signals. The second computer 26 converts the calculated O2 concentration value to a corresponding NO concentration value. The NO concentration value is transferred to the engine control unit 27. The engine control unit 27 employs the air/fuel ratio value transferred thereto from the first computer 25 and the NO concentration value transferred thereto from the second computer 26 to control the engine 10. Since the first computer 25 transfers the air/fuel ratio value to the engine control unit 27, there is no need for an additional oxygen sensor used in monitoring the air/fuel ratio of the air-fuel mixture supplied to the engine.

The NOx concentration measuring apparatus includes a sensor retainer 30 having an externally threaded end portion 31 threadedly engaged with an externally threaded opening 16 formed in an exhaust manifold wall 14. The sensor retainer 30 has a gas inlet passage 32 which enxtends through the sensor retainer 30 in the direction of the length of the sensor retainer 30 and in a direction substantially perpendicular to the direction of the exhaust gases flow through the exhaust manifold 12. Since the opening 16 communicates with the exhaust manifold 12, this results in the gas inlet passage 32 opening at its one end into the exhaust manifold 12. The other end of the gas inlet passage 32 is connected through a conduit 42 to a suction port of a suction pump 50. The suction pump 50 has another suction port connected to a conduit 43 and a discharge port connected to one end of a conduit 44. The other end of the conduit 44 opens into the exhaust manifold 12.

Figure 3:
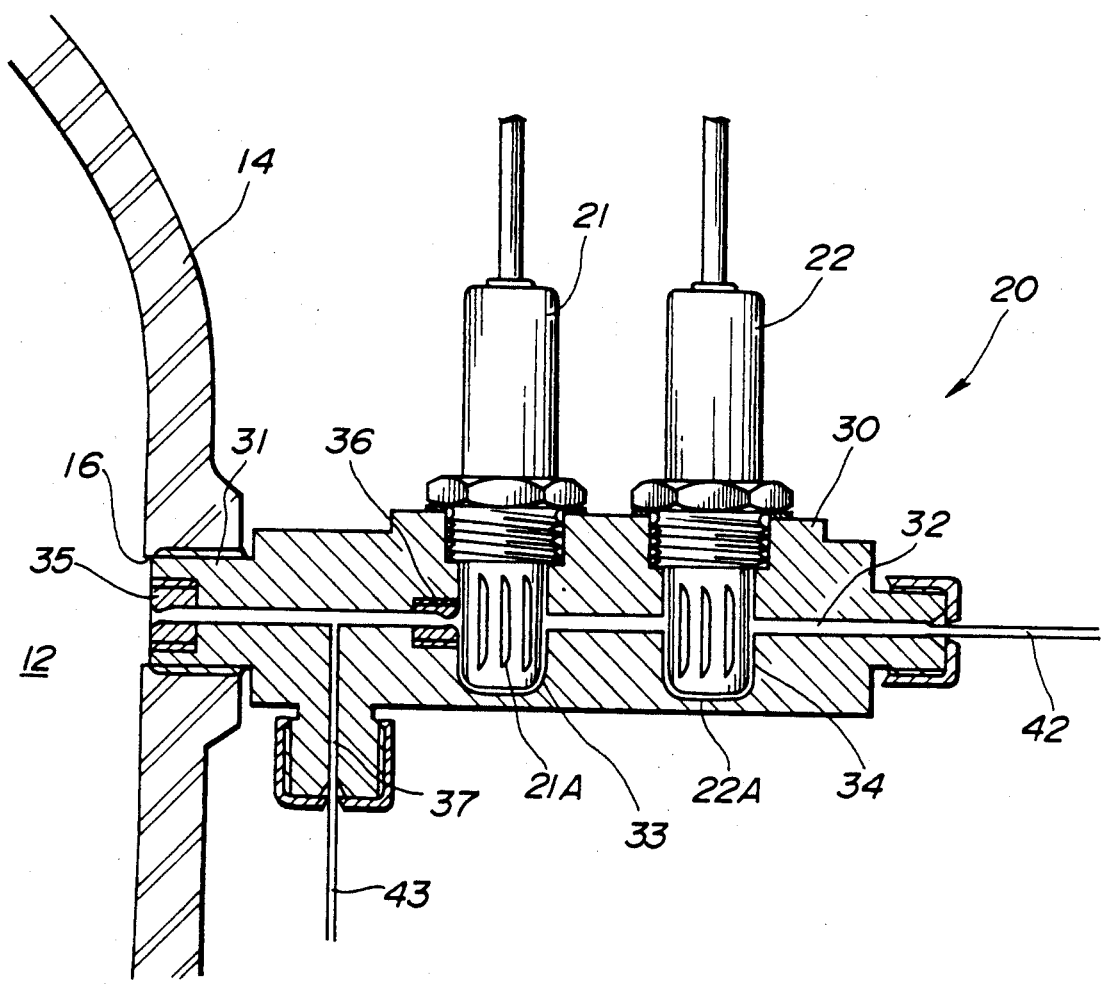
FIG. 3 is an enlarged sectional view of the sensor retainer.

Referring to FIG. 3, the sensor retainer 30 is formed with a first pocket 33 for the receipt of the first sensor 21 and a second pocket 34 for the receipt of the second sensor 22. The first and second pockets 33 and 34 communicate with each other through the gas inlet passage 32. The air inlet passage 32 has a first restricted orifice 35, the area of whose opening determines the degree of reduction of the exhaust gas pressure introduced from the exhaust manifold 12 into the gas inlet passage 32. The air inlet passage 32 also has a second restricted orifice 36 located in the air inlet passage 32 somewhere upstream of the first pocket 33. The area of the opening of the second orifice 36 determines the degree of reduction of the gas pressure introduced into the first pocket 33. A branched passage 37 opens at its one end into the gas inlet passage 32 somewhere between the first and second orifices 35 and 36 and it is connected at the other end thereof through the conduit 43 to the suction pump 50 (FIG. 1). The numeral 21A designates a louver door provided upstream of the diffusion chamber of the first sensor 21, and the numeral 22A designates a louver door provided upstream of the diffusion chamber of the second sensor 22.

The operation is as follows. When the suction pump 50 is operating, exhaust gases are introduced from the exhaust manifold 12 through the first orifice 35 into the gas inlet passage 32. The first orifice 35 provides an exhaust gas pressure reduction ranging from about 50 mmHg to about 100 mmHg with respect to the exhaust manifold pressure. Most of the exhaust gases are sucked through the branched passage 37 and the conduit 43 to the suction pump 50. However, some of the exhaust gases are introduced through the second orifice 36 into the diffusion chamber of the first sensor 21 placed in the first pocket 33. The second orifice 36 provides an additional exhaust gas pressure reduction ranging from about 200 mmHg to 400 mmHg. The exhaust gas are then introduced into the diffusion chamber of the second sensor 22 placed in the second pocket 34 and hence through the conduit 42 to the suction pump 50. The suction pump 50 discharges the exhaust gases, which are introduced therein from the conduits 42 and 43, through the conduit 44 into the exhaust manifold 12.

The first and second orifices 35 and 36 can reduce the width of the range in which the pressure of the exhaust gases introduced into the diffusion chambers of the first and second sensors 21 and 22 to several mmHgs when the width of the range in which the exhaust manifold pressure varies is several hundreds of mmHg. Thus, the first and second orifices 35 and 36 are effective to prevent momentary fluctuations in the exhaust manifold pressure from affecting the accuracy of measurement of the first and second sensors 21 and 22.

Figure 4:
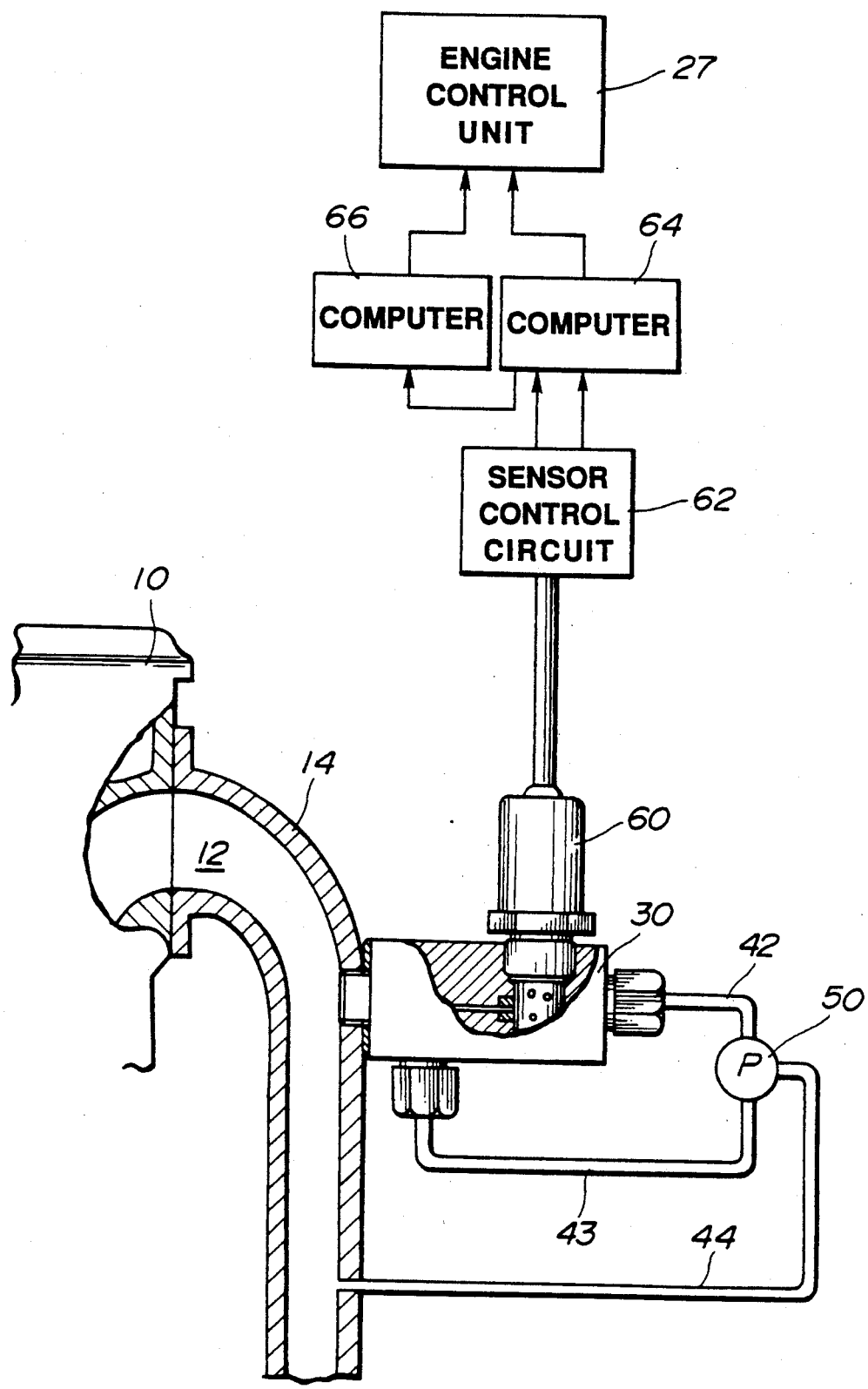
FIG. 4 is a schematic diagram showing a second embodiment of the NOx measuring apparatus of the invention.

Referring to FIG. 4, there is shown a second embodiment of the NOx concentration measuring apparatus of the invention. The arrangement of FIG. 4 utilizes a number of components previously described, and like reference numerals in FIG. 4 indicate like parts as described with reference to FIG. 1. The chief difference between FIG. 4 and the first described embodiment is that the measuring apparatus includes a sensor 60 having two sensors incorporated in a single casing. These sensors, which are substantially the same as the first and second sensors 21 and 22 of FIG. 1, are connected to a sensor control circuit 62. The sensor control circuit 62 produces a first sensor signal having a value proportional to the sensed O2 concentration, as described in connection with the first sensor 21, and a second sensor signal having a value proportional to the sensed O2 concentration, as described in connection with the second sensor 22. The first and second sensor signals are fed to a first computer 64. The first computer 64 calculates an O2 concentration value, which is one-half of the NO concentration, as a function of a difference between the values of the first and second sensor signals. The first computer 64 converts the calculated O2 concentration value to a corresponding NO concentration value and transfers the NO concentration value to the engine control unit 27. The first computer 64 also transfers the first sensor signal to a second computer 66 which calculates a value of he air/fuel ratio of the exhaust gases based on the value of the first sensor signal transferred thereto from the first computer 64 and transfers the calculated air/fuel ratio value to the engine control unit 27. The engine control unit 27 employs the NO concentration value transferred thereto from the first computer 64 and the air/fuel ratio value transferred thereto from the second computer 66 to control the engine 10. Since the second computer 66 transfers the air/fuel ratio value to the engine control unit 27, there is no need for an additional oxygen sensor used in monitoring the air/fuel ratio of the air-fuel mixture supplied to the engine. Since the first and second sensors included in the sensor 60 have the same characteristics, it is possible to improve the accuracy of measurement of the NOx measuring apparatus. Furthermore, the measuring apparatus of this embodiment consumes less space for equipment than the measuring apparatus of the first described embodiment.

Although the invention has been described in connection with engine exhaust gases, it should be understood that the invention is also applicable to measure NOx concentrations of other gases.

What is claimed is:

1. An apparatus for measuring an NOx concentration of gases to be measured, comprising:

a first sensor sensitive to oxides of nitrogen for resolving oxides of nitrogen at low oxygen partial pressures, the first sensor including an electrochemical cell containing an oxygen ion conductive electrolyte layer having at least two electrodes disposed on the opposite surfaces thereof for producing a first sensor signal indicative of an oxygen partial pressure of the gases introduced into the electrochemical cell;

a second sensor insensitive to oxides of nitrogen, the second sensor including an electrochemical cell containing an oxygen ion conductive electrolyte layer having at least two electrodes disposed on the opposite surfaces thereof for producing a second sensor signal indicative of an oxygen partial pressure of the gases introduced into the electrochemical cell;

means connected to the first and second sensors for calculating an NOx concentration based on the first and second sensor signals;

a first passage for introducing gases into the electrochemical cells of the first and second sensors;

first and second restricted orifices provided in the first passage upstream of the first and second sensors for restricting a gas flow to the first and second sensors;

a second passage connected to the first passage between the first and second orifices; and a suction pump connected to the first passage downstream of the first and second sensors for producing a suction vacuum in the first passage and to the second passage for producing a suction vaccum in the second passage.

2. An apparatus for measuring an NOx concentration of exhaust gases discharged into an exhaust manifold from an internal combustion engine, the apparatus comprising:

a first sensor sensitive to oxides of nitrogen for resolving oxides of nitrogen at low oxygen partial pressures, the first sensor including an electrochemical cell containing an oxygen ion conductive electrolyte layer having at least two electrodes disposed on the opposite surfaces thereof for producing a first sensor signal indicative of an oxygen partial pressure of the exhaust gases introduced into the electrochemical cell;

a second sensor insensitive to oxides of nitrogen, the second sensor including an electrochemical cell containing an oxygen ion conductive eletrolyte layer having at least two electrodes disposed on the opposite surfaces thereof for producing a second sensor signal indicative of an oxygen partial pressure of the exhaust gases introduced into the electrochemical cell;

means connected to the first and second sensors for calculating and NOx concentration based on the first and second sensor signals;

a first passage opening into the exhaust manifold for introducing exhaust gases into the electrochemical cells of the first and second sensors;

first and second restricted orifices provided in the first passage upstream of the first and second sensors for restricting a gas flow to the first and second sensors;

a second passage connected to the first passage between the first and second orifices; and a suction pump connected to the first passage downstream of the first and second sensors for producing a suction vacuum in the first passage, the suction pump being connected to the second passage for producing a suction vacuum in the second passage.

3. The apparatus as claimed in claim 2, wherein the calculating means includes means for calculating an air/fuel ratio value of an air-fuel mixture supplied to the engine based on the first sensor signal.

* * * * *